United States Patent

Seward et al.

[11] Patent Number: 5,561,130
[45] Date of Patent: Oct. 1, 1996

[54] AZACYCLIC COMPOUNDS

[75] Inventors: Eileen M. Seward, Bishops Stortford; Christopher J. Swain, Duxford, both of United Kingdom

[73] Assignee: Merck Sharp & Dohme Limited, Hoddesdon, England

[21] Appl. No.: 379,622

[22] PCT Filed: Jul. 20, 1993

[86] PCT No.: PCT/GB93/01525

§ 371 Date: Jan. 24, 1994

§ 102(e) Date: Jan. 24, 1994

[87] PCT Pub. No.: WO94/02461

PCT Pub. Date: Feb. 3, 1994

[30] Foreign Application Priority Data

| Jul. 28, 1992 | [GB] | United Kingdom | 9216065 |
| Jul. 31, 1992 | [GB] | United Kingdom | 9216304 |
| Nov. 27, 1992 | [GB] | United Kingdom | 9224918 |
| Dec. 14, 1992 | [GB] | United Kingdom | 9226058 |

[51] Int. Cl.$^6$ .............. A61K 31/445; A61K 31/535; C07D 211/42; C07D 413/06
[52] U.S. Cl. .............. 514/235.5; 514/252; 514/326; 514/327; 544/130; 544/365; 546/194; 546/214; 546/221
[58] Field of Search .............. 544/130; 546/221; 514/235.5

[56] References Cited

U.S. PATENT DOCUMENTS

| 4,996,327 | 2/1991 | Merkle et al. |
| 5,128,480 | 7/1992 | Merkle et al. |
| 5,459,270 | 10/1995 | Williams et al. ............ 546/221 |

FOREIGN PATENT DOCUMENTS

| 1141390 | 2/1983 | Canada . |
| 20964 | 1/1981 | European Pat. Off. . |
| 366327 | 5/1990 | European Pat. Off. . |
| 402722 | 12/1990 | European Pat. Off. . |
| 0436334 | 7/1991 | European Pat. Off. . |
| 0499313 | 2/1992 | European Pat. Off. . |
| 474037 | 3/1992 | European Pat. Off. . |
| 0528495 | 2/1993 | European Pat. Off. . |

OTHER PUBLICATIONS

Advances in Heterocyclic Chemistry, Katritzky, vol. 6, 1966.
Pyrazoles, Pyrazolines, Pyrazolidines, Idazoles and Condensed Rings, Behr et al., The Chemistry of Heterocyuclic Compounds, 1967.
Desai, et al., J. Med. Chem. 35(26) pp. 4911–4913 (1992) "Discovery of a Potent Substance P Antagonist: Recognition of the Key Molecular Determinant".
Chem. Abstracts, 100, Abstract No. 192245m (1984) Columbus, Ohio, US.
J. Chem. Soc., Perkin Trans 1, 1, pp. 29–39 (1984).

Primary Examiner—Robert W. Ramsuer
Attorney, Agent, or Firm—J. Eric Thies; David L. Rose

[57] ABSTRACT

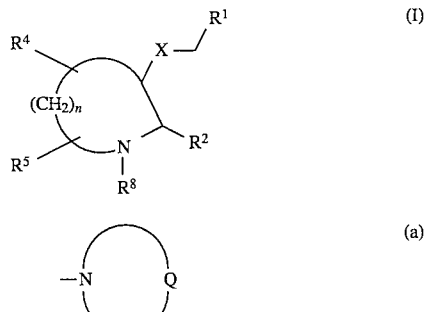

Compounds of Formula (I), and salts and prodrugs thereof, wherein n is 1, 2 or 3; X represents O or S; $R^1$ is optionally substituted phenyl; $R^2$ is aryl or heteroaryl; $R^4$ and $R^5$ are independently H, halo, $C_{1-6}$alkyl, oxo, $CH_2OR^a$, $CO_2R^a$ or $CONR^aR^b$; $R^8$ represents $C(COOR^a)_2$, $C(CONR^aR^b)_2$ or $C_{1-6}$alkyl substituted by $C(=NR^a)NR^bNR^cCO_2R^d$, $CONHNR^aR^b$, $C(S)NR^aR^b$, $CONR^aC_{1-6}$alkyl$R^{12}$, $CONR^{13}C_{2-6}$alkynyl, $CONR^{13}C_{2-6}$alkenyl, $COCONR^aR^b$, $CONR^aC(NR^b)NR^cR^d$, $CONR^{13}SO_2R^a$, $SO_2NR^{13}COR^a$, $CONR^a$heteroaryl or $COR^q$; $R^a$, $R^b$, $R^c$ and $R^d$ are each H, $C_{1-6}$alkyl, phenyl or trifluoromethyl. $R^{12}$ represents $OR^a$, $CONR^aR^b$ or heteroaryl; $R^{13}$ represents H or $C_{1-6}$alkyl; and $R^q$ represents a group (a) where Q represents the residue of a non-aromatic azacyclic or azabicyclic ring system; are tachykinin antagonists useful in therapy.

14 Claims, No Drawings

AZACYCLIC COMPOUNDS

This application is a 371 of PCT/GB 93/01525 filed Jul. 20, 1993.

This invention relates to a class of azacyclic compounds, which are useful as tachykinin antagonists. More particularly, the compounds of the invention comprise an azacyclic ring system substituted by an arylmethyloxy or arylmethylthio moiety.

The tachykinins are a group of naturally-occurring peptides found widely distributed throughout mammalian tissues, both within the central nervous system and in the peripheral nervous and circulatory systems. The structures of three known mammalian tachykinins are as follows:

Substance P;

Neurokinin A; and

Neurokinin B.

Evidence for the usefulness of tachykinin receptor antagonists in pain, headache, especially migraine, Alzheimer's disease, multiple sclerosis, attenuation of morphine withdrawal, cardivascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, J. Auton. Pharmacol. (1993) 13, 23–93. Tachykinin antagonists are also believed to be useful in allergic conditions [Hamelet et al Can. J. Pharmacol. Physiol. (1988) 66 1361–7], immunoregulation [Lotz et al Science (1988) 241 1218–21 and Kimball et al, J. Immunol. (1988) 141 (10) 3564–9], and as anticonvulsants [Garant et al., Brain Research (1986) 382 372–8]. Tachykinin antagonists may also be useful in the treatment of small cell carcinomas, in particular small cell lung cancer (SCLC) [Langdon et al., Cancer Research (1992) 52, 4554–7].

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent application no. 0 436 334), conjuctivitis, vernal conjunctivitis, contact dermatitis, atropic dermatitis, urticaria, and other eczematoid dermatitis (European patent application no. 0 394 989) and emesis (European patent application no. 0 533 280).

European patent application no. 0 436 334 discloses 4- to 7-membered azacyclic compounds substituted at the 3-position by a substituted amino moiety. The compounds are said to be tachykinin antagonists.

The present invention provides a compound of formula (I), or a salt or prodrug thereof:

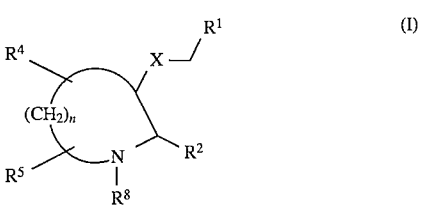

wherein n is 1, 2 or 3;

X represents O or S;

$R^1$ represents phenyl optionally substituted by 1, 2 or 3 groups selected from $C_{1-6}$alkyl, $C_{2-6}$ alkenyl, $C_{2-6}$alkynyl, halo, cyano, nitro, trifluoromethyl, trimethylsilyl —$OR^a$, $SR^a$, $SOR^a$, $SO_2R^a$, —$NR^aR^b$, —$NR^aCOR^b$, —$NR^aCO_2R^b$, —$CO_2R^a$ and —$CONR^aR^b$;

$R^2$ represents aryl selected from phenyl and naphthyl; heteroaryl selected from indazolyl, thienyl, furyl, pyridyl, thiazolyl, tetrazolyl and quinolyl; benzhydryl; or benzyl; wherein each aryl or heteroaryl moiety may be substituted by $C_{1-6}$alkyl, $C_{1-6}$alkoxy, halo or trifluoromethyl;

$R^4$ and $R^5$ may be present on any available carbon atom of the azacyclic ring and each independently represent H, halo, $C_{1-6}$alkyl, oxo, $CH_2OR^a$, $CO_2R^a$ or $CONR^aR^b$;

$R^8$ represents $C(COOR^a)_2$, $C(CONR^aR^b)_2$ or $C_{1-6}$alkyl substituted by $C(=NR^a)NR^bNR^cCO_2R^d$, $CONHNR^aR^b$, $C(S)NR^aR^b$, $CONR^aC_{1-6}$alkyl$R^{12}$, $CONR^{13}C_{2-6}$alkynyl, $CONR^{13}C_{2-6}$alkenyl, $COCONR^aR^b$, $CONR^aC(NR^b)NR^cR^d$, $CONR^{13}SO_2R^a$, $SO_2NR^{13}COR^a$, $CONR^a$heteroaryl or $COR^q$;

$R^a$, $R^b$, $R^c$ and $R^d$ each independently represent H, $C_{1-6}$alkyl, phenyl or trifluoromethyl.

$R^{12}$ represent $OR^a$, $CONR^aR^b$ or heteroaryl;

$R^{13}$ represents H or $C_{1-6}$alkyl; and $R^q$ represents a group

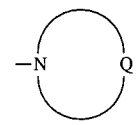

where Q represents the residue of a non-aromatic azacyclic or azabicyclic ring system.

As used herein, the definition of each expression, when it occurs more than once in any structure, is intended to be independent of its definition elsewhere in the same structure.

The alkyl, alkenyl and alkynyl groups referred to with respect to the above formula may represent straight, branched or cyclic groups, or combinations thereof. Thus, for example, suitable alkyl groups include methyl, ethyl, n- or iso-propyl, n-, see-, iso- or tert-butyl, cyclopropyl, cyclobutyl, cyclopentyl or cyclohexyl, and cycloalkyl-alkyl groups such as cyclopropylmethyl; suitable alkenyl groups include vinyl and allyl; and suitable alkynyl groups include propargyl.

The term "halo" as used herein includes fluoro, chloro, bromo and iodo, especially chloro and fluoro.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The compounds according to the invention may exist both as enantiomers and as diastereomers. In particular, the relative orientation of the 2- and 3-substituents in the azacyclic ring may give rise to cis and trans diastereoisomers, of which the cis stereochemistry is preferred. It is to be understood that all such isomers and mixtures thereof are encompassed within the scope of the present invention.

One subgroup of compounds according to the invention is represented by compounds of formula (I) wherein $R^4$ and $R^5$ each independently represent H, halo, $C_{1-6}$alkyl, oxo, $CO_2R^{10}$ or $CONR^{10}R^{11}$: $R^8$ represents $C_{1-6}$alkyl substituted by a group selected from $CONHNR^aR^b$, $C(S)NR^aR^b$, $CONR^aC_{1-6}$alkyl$R^{12}$, $CONR^{13}C_{2-6}$alkynyly, $CONR^{13}C_{2-6}$alkenyl, $COCONR^aR^b$, $CONR^aC$ $(NR^b)N$-$R^aR^b$, and $CONR^a$heteroaryl; and salts and prodrugs thereof.

A further subgroup of compounds according to the invention is represented by compounds of formula (Ia):

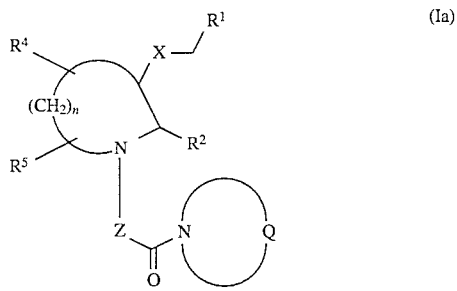

(Ia)

wherein n, X, $R^1$ and $R^2$ are as defined for formula (I); Q is the residue of an azacyclic or a bridged azabicyclic ring system;

Z represents an alkyl chain of 1, 2, 3, 4, 5 or 6 carbon atoms; and $R^4$ and $R^5$ each independently represent H, halo, $C_{1-6}$alkyl, oxo, $CO_2R^a$ or $CONR^aR^b$; and salts and prodrugs thereof.

Preferably n is 2 or 3, more preferably 3.

Preferably X represents O.

Preferably $R^1$ represents substituted phenyl. When $R^1$ is substituted phenyl suitable substituents include nitro, trifluoromethyl, trimethylsilyl, bromo, chloro, fluoro, iodo, cyano, $C_{1-6}$alkyl such as methyl, ethyl, i-propyl, i-butyl, t-butyl and cyclopropyl, $C_{2-6}$alkenyl such as vinyl, $C_{1-6}$alkoxy such as methoxy, ethoxy and i-propoxy, phenoxy, amino, carboxamido and carbonylmethoxy. Preferably $R^1$ represents phenyl substituted by one or more groups selected from $C_{1-4}$alkyl, such as methyl and t-butyl, trifluoromethyl and halo such as iodo, bromo chloro and fluoro.

Suitably $R^1$ represents monosubstituted phenyl, such as 3-substituted phenyl or, preferably, disubstituted phenyl, such as 3,5-disubstituted phenyl. Preferably $R^1$ represents phenyl substituted at the 3-position by trifluoromethyl or a $C_{1-6}$alkyl group such as t-butyl, or 3,5-disubstituted phenyl wherein the substituents are independently selected from trifluoromethyl, chloro, fluoro, methyl and t-butyl. Particularly preferred is 3,5-bis(trifluoromethyl)phenyl.

Suitably $R^2$ represents benzhydryl or optionally substituted phenyl, such as phenyl optionally substituted by halo such as fluoro or chloro, preferably in the 3-position. Preferably $R^2$ represents unsubstituted phenyl or unsubstituted benzhydryl, more preferably unsubstituted phenyl.

Suitable values for $R^4$ and $R^5$ include H, $C_{1-6}$alkyl, especially methyl, hydroxymethyl and oxo. The substituents $R^4$ and $R^5$ may be located on any available carbon atom of the azacyclic ring including, except in the case where the substituent $R^4$ or $R^5$ in question represents oxo, C-2 and C-3. Preferably at least one of $R^4$ and $R^5$ represents H. In one preferred group of compounds $R^4$ and $R^5$ both represent H. In a further preferred group of compounds one of $R^4$ and $R^5$ is H and the other of $R^4$ and $R^5$ is methyl, preferably 2-methyl.

Suitable values for $R^8$ include $C(COO(C_{1-6}alkyl))_2$, such as $C(COOCH_3)_2$, $C(CONH_2)_2$ and $C_{1-6}$alkyl, preferably $C_{1-4}$alkyl, more preferably $CH_2$ or $CH(CH_3)$, substituted by $C(=NH)NHNHCO_2C_{1-6}$alkyl, $CONHNH_2$, $COCONH_2$, $CONHC(NH)NH_2$, $C(S)NH_2$, $CONR^{13}C_{2-6}$alkynyl, $CONR^aC_{1-6}$alkyl$C_{1-6}$alkoxy, $CONHSO_2C_{1-6}$alkyl, $CONR^aC_{1-6}$alkylheteroaryl, $CONR^a$heteroaryl or $COR^q$.

When $R^8$ represents $C_{1-6}$alkyl subsituted by $CONR^aC_{1-6}$alkylheteroaryl or $CONR^a$heteroaryl, the heteroaryl moiety will suitably be selected from thienyl, furyl, pyridyl, thiazolyl, tetrazolyl, pyrrolyl, pyrazolyl, pyrazinyl, pyrimidinyl, pyridazinyl, triazinyl, quinolyl, triazolyl, oxazolyl, oxadiazolyl, thiadiazolyl, isoxazolyl, isothiazolyl, benzoxazolyl, imidazolyl, benzimidazolyl, benzothiophenyl, benzofuranyl, and indolyl, preferably, furyl and pyridyl. The heteroaryl moiety may be optionally substituted. Suitable substituents include one or more of $C_{1-6}$alkyl, $C_{1-6}$alkoxy, phenyl, oxo, thioxo, halo, trifluoromethyl, $NR^aR^b$, $NR^aCOR^b$, $CONR^aR^b$, $SR^a$, $SO_2R^a$, $CO_2R^a$ and $CH_2OR^a$, where $R^a$ and $R^b$ are as previously defined.

The non-aromatic azacyclic or azabicyclic ring system of which Q forms the residue may contain, in addition to the nitrogen atom through which the ring is linked to the carbonyl moiety of the group $COR^q$, a further heteroatom selected from O and S, or a group $NR^{18}$, where $R^{18}$ is H or $C_{1-6}$alkyl.

When Q forms the residue of an azacyclic ring system, the azacyclic ring system will suitably contain from 5 to 9 ring atoms, preferably 5, 6 or 7 ring atoms, more preferably 6.

When Q forms the residue of an azabicyclic ring system, the azabicyclic ring system will suitably contain from 7 to 10 ring atoms, preferably 6 or 8 ring atoms, more preferably 8.

Suitable examples of the ring system of which Q forms the residue include pyrrolidinyl, piperidinyl, morpholinyl, piperazinyl, N-methylpiperazinyl azabicyclo[2.2.2]octanyl and azabicyclo[3.2.2]nonyl, preferably piperidyl, morpholinyl or N-methylpiperazinyl, more preferably morpholinyl or N-methylpiperazinyl.

A preferred subgroup of compounds according to the invention is represented by compounds of formula (Ib), and salts and prodrugs thereof.

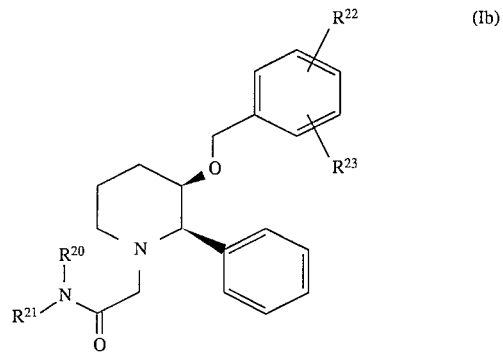

(Ib)

wherein $R^{20}$ represents H or $C_{1-6}$alkyl, preferably H or methyl;

$R^{21}$ represents $NH_2$, $C(=NH)NH_2$, $C_{2-6}$alkynyl or $C_{1-6}$alkyl substituted by $C_{1-6}$alkoxy, such as methoxy or heteroaryl, such as furyl or pyridyl; or $R^{20}$ and $R^{21}$ together with the nitrogen atom to which they are attached form a group

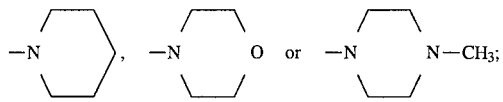

$R^{22}$ and $R^{23}$ independently represent H $C_{1-6}$alkyl, $C_{2-6}$alkenyl, $C_{2-6}$alkynyl, halo, cyano, nitro, trifluoromethyl trimethylsilyl, $OR^a$, $SR^a$ $SOR^a$, $SO_2R^a$, $NR^aR^b$, $NR^aCOR^b$, $NR^aCO_2R^b$, $COR^a$ or $CONR^aR^b$, where $R^a$ and $R^b$ are as previously defined.

For use in medicine, the salts of the compounds of formula (I) will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, sulphuric acid, oxalic acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Thus, for example, when both $R^1$ and $R^2$ are other than hydrogen, the nitrogen atom to which they are attached may be further substituted to give a quaternary ammonium salt. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The present invention accordingly provides compounds of formula (I) and their pharmaceutically acceptable salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The compounds according to the invention may exist both as enantiomers and as diastereomers. It is to be understood that all such isomers and mixtures thereof are encompassed within the scope of the present invention.

The substance P antagonising activity of the compounds described herein was evaluated using the human NK1R assay described in published European patent application no. 0 528 495. The method essentially involves determining the concentration of the test compound required to reduce by 50% the amount of. radiolabelled substance P binding to human NK1R, thereby affording an $IC_{50}$ value for the test compound. The compounds of Examples 1–10, for example, were found to have $IC_{50}$ values less than 100 nM.

The invention also provides pharmaceutical compositions comprising a compound of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or topical administration including administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are adminsitered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

For topical administration, for example as a cream, ointment or lotion, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as MS and ALS and other neuropathological disorders such as peripheral neuropathy, including diabetic and chemotherapy-induced neuropathy, and postherpetic and other neuralgias; small cell carcinomas such as small cell lung cancer; respiratory diseases, particularly those associated with excess mucus secretion such as chronic obstructive airways disease, bronchopneumonia, chronic bronchitis, cystic fibrosis and asthma, and bronchospasm; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; emesis, including acute, delayed and anticipatory emesis, for example, induced by chemotherapy, radiation, toxins, pregnancy, vestibular disorders, surgery, migraine and variations in intercranial pressure; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and especially migraine.

The present invention further provides a compound of formula (I), or a salt or prodrug thereof, for use in therapy.

In the treatment of conditions involving actions of tachykinins released physiologically in response to noxious or other stimuli, a suitable dosage level is about 0.001 to 50 mg/kg per day, preferably about 0.005 to 10 mg/kg per day, and especially about 0.005 to 5 mg/kg per day. The compounds may be administered on a regimen of 1 to 4 times per day, preferably once daily.

According to a further or alternative aspect, the present invention provides a method of treatment of a human or animal subject suffering from or susceptible to a condition characterised by the presence of an excess of tachykinin which method comprises administering to a human or animal subject in need of such treatment an effective amount of a compound of formula (I), or a salt or prodrug thereof.

The present invention also provides the use of a compound of formula (I), or a salt or prodrug thereof, for the manufacture of a medicament for the treatment of conditions characterised by the presence of an excess of tachykinins.

According to one general process (A), the compounds according to the invention may be prepared by a process which comprises reacting a compound of formula

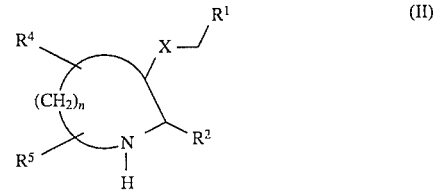

(II)

wherein $R^1$, $R^2$, $R^4$, $R^5$, X and n are as defined for formula (I) above, with a reagent suitable to introduce the group $R^8$, for example, a halide or acyl halide, or corresponding mesylate or rosylate, of formula $R^8$-L, where L represents halo, such as chloro, bromo or iodo, methylsulphonate or p-toluenesulphonate, or any other suitable leaving group, in the presence of a base.

Suitable bases of use in the reaction include inorganic bases such as alkali metal carbonates, for example, potassium carbonate.

Conveniently the reaction is effected in a suitable organic solvent, for example, dimethylformamide.

According to a second process (B), compounds of formula (I) wherein $R^8$ represents $C_{1-6}$alkyl subsituted by $CONR^aC_{1-6}$alkyl$R^{12}$, $CONR^{13}C_{2-6}$alkenyl, $CONR^{13}C_{2-6}$alkynyl, $CONR^aC(NR^b)NR^cR^9$, $CONR^a$heteroaryl or $COR^q$ may be prepared by reaction of an intermediate of formula (III):

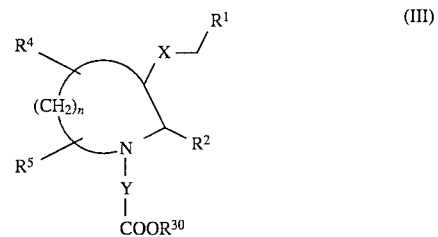

(III)

wherein $R^1$, $R^2$, $R^4$, $R^5$, X and n are as defined for formula (I), $R^{30}$ is H or alkyl and Y represents $C_{1-6}$alkylidene with an amine of formula $HNR^aC_{1-6}$alkyl$R^{12}$, $HNR^{13}C_{2-6}$alkenyl, $HNR^{13}C_{2-6}$alkynyl, $HNR^aC(NR^b)N$-$R^cR^9$, $HNR^a$heteroaryl or

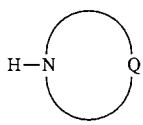

in the presence of a base.

Suitable bases of use in the reaction include organic bases such as tertiary amines, for example, triethylamine.

The reaction is preferably effected in the presence of a coupling agent such as, for example, 1-(3-dimethylaminopropyl)-3-ethylcarbodiimide hydrochloride.

The reaction is conveniently effected in a suitable organic solvent, such as an ether, for example, tetrahydrofuran, suitably at ambient temperature.

Compounds of formula (I) may also be prepared from different compounds of formula (I) by interconversion processes. In particular, interconversion processes may be used to vary the group $R^8$.

Intermediates of formulae (II) and (III) may be prepared as described in published European patent application no. 0 528 495.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. For example, any suitable intermediates may be resolved into their component enantiomers by standard techniques, such as the formation of diastereomeric esters or amides, followed by chromatographic separation or separation by fractional crystallization and removal of the chiral auxiliary. The diastereomeric intermediates can then be used to prepare optically pure compounds of formula (I).

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art, The following Examples illustrate the preparation of compounds according to the invention.

DESCRIPTION 1 cis-3-((3,5-Bis(trifluoromethyl)phenyl)methyloxy)-2-phenyl piperidine hydrochloride salt a) A solution of methyl 4-nitrobutyrate (23g) and benzaldehyde (16ml) in acetic acid (39ml) containing ammonium acetate (12.12g) was heated at reflux under nitrogen for 2h. The reaction mixture was cooled to 5° C., whereby a pale-yellow solid crystallised. This was isolated by filtration, then dissolved in dichloromethane, washed cautiously with saturated aqueous sodium bicarbonate solution (2×), then dried ($MgSO_4$) and concentrated to leave a yellow solid. Recrystallisation from ethyl acetate provided 5-nitro-2-oxo-6-phenylpiperidine (12.5g) as a crystalline, white solid. $^1$H NMR ($CDCl_3$) δ7.46–7.26 (m), 6.0 (br s), 5.24 (dd, J=1.4, 7.0Hz), 4.70 (m), 2.70–2.50 (m), 2.38–2.24 (m).

b) Potassium t-butexide (1.68g) was added to a solution of 5-nitro-2-oxo-6-phenylpiperidine (3g) in a mixture of dichloromethane (50ml) and methanol (50ml) and the mixture was cooled to −78° C. under nitrogen. Ozone was bubbled through the solution for 3h. A yellow-green solution resulted, and TLC indicated no starting material remained. The reaction mixture was purged with oxygen for 5 min to remove excess ozone, then dimethylsulfide (7ml) was added and the reaction mixture was allowed to warm to 23° C. The solvent was removed in vacuo, and the residue was partitioned between dichloromethane and water. The layers were separated, and the aqueous phase was extracted twice with dichloromethane. The combined organic extracts were washed with brine, then dried ($K_2CO_3$) and concentrated to leave a yellow solid.

This crude material was slurried in dry THF and added to lithium aluminium hydride (1M in THF, 50 ml) then heated at reflux for 12h. After cooling to 23° C., the reaction mixture was quenched by the cautious addition of water (dropwise) under nitrogen, then 2M sodium hydroxide. The mixture was filtered through a pad of Hyflo, the filtrate was washed with brine, then dried ($K_2CO_3$) and concentrated to leave a yellow solid. Purification by silica-gel chromatography ($CH_2Cl_2$/MeOH/$NH_3$ 97:3:1 then $CH_2Cl_2$/MeOH 95:5) provided 3-hydroxy-2-phenylpiperidine as a ca 4:1 mixture of cis- and trans-isomers respectively. $^1$H NMR ($CDCl_3$) 7.44–7.20 (m), 3.84 (2), 3.76 (s), 3.54 (m), 3.4 (s), 3.3 (d, J=8Hz), 3.26 (m), 3.04 (m) 2.78 (ddd, J=2.9, 11.9, 11.9Hz), 2.70 (ddd, J=2.9, 11.9, 11.9Hz), 2.18–1.78 (m), 1.48 (m). MS (EI) m/z 177 ($M^+$).

c) Di-t-butyldicarbonate (1.36g) was added to a solution of 3-hydroxy-2-phenylpiperidine (1 g) in dichloromethane (8 ml) under nitrogen and the mixture stirred at 23° C. for 3h. The solvent was removed in vacuo, and the residue purified by silica-gel chromatography ($CH_2Cl_2$/MeOH/$NH_3$ 97:3:0.5) to provide cis- and trans-1-t-butyloxycarbonyl-3-hydroxy-2-phenylpiperidine (1.4 g) as a clear, viscous oil. $^1$H NMR ($CDCl_3$) δ7.50–7.42 (m), 7.40–7.14 (m), 5.36 (d, J=5.6Hz), 4.50 (m), 4.44 (m), 4.12–3.92 (m), 3.02 (ddd, J=3.0, 12.5, 12.5 Hz), 2.87 (ddd, J=3.0, 12.5, 12.5 Hz), 1.88–1.66 (m), 1.46 (s), 1.36 (s).

d) To a cooled (0° C.) solution of 1-t-butyloxycarbonyl-3-hydroxy-2-phenylpiperidine (1.4g) in dry dimethylforamide (5ml) was added sodium hydride (80% dispersion in mineral oil; 182 mg). The cooling bath was removed and the reaction mixture stirred at 23° C. for 30 min. A solution of 3,5-bis(trifluoromethyl) benzyl bromide (1.87 g) in dry dimethylformamide (1 ml) was added and stirring was continued for 2 h at room temperature. The mixture was diluted with water (100 ml) and extracted with ethyl acetate (3×40 ml). The combined organic extracts were washed with brine (1×30 ml), dried ($MgSO_4$) and evaporated to yield a pale yellow oil. Purification by chromatography on silica using gradient elution of hexane in ethyl acetate (9:1–4:1) afforded the product cis- 1-t-butyloxycarbonyl-3-((3,5, bis (trifluoromethyl)phenyl)methyloxy)-2,-phenylpiperidine (350 mg) as a dear viscous oil. $^1$H NMR (250MHz, $CDCl_3$) δ7.77 (1H, s, ArH), 7.71 (2H, s, ArH), 7.53–7.57 (2H, m, ArH), 7.2–7.4 (3H, m, ArH), 5.70 (1H, br d, app. J=7.0Hz, NCHPh), 4.73 (2H, brs, $OCH_2$), 3.84–3.98 (2H, m, NCHC HO+NCHH), 2.77 (1H, ddd, J=13.0, 13.0, 3.0Hz), NCH H), 2.00 (2H, mc, $CH_2$), 1.6–1.8 (2H, m, $CH_2$), 1.40 (9H, s, $C(CH_3)_3$).

e) Trifluoroacetic acid (3 ml) was added to the product of (d) above (800 mg) under nitrogen and the resulting solution was stirred for 1 h. Excess trifluoroacetic acid was removed in vacuo and the residue was partitioned between 2M sodium hydroxide and dichloromethane. The organic phase was washed with brine, dried (MgSO$_4$) and evaporated to afford a colourless oil. Purification on silica (dichloromethane in methanol, 98:2–95:5) afforded the product cis-3-((3,5-bis(trifluoromethyl)phenyl) methyloxy-2-phenylpiperidine (360 mg) as a colourless oil. $^1$H NMR (360 MHz, CDCl$_3$) δ7.78 (1H, s, ArH), 7.44 (2H, s, ArH), 7.18–7.38 (5H, s, ArH), 4.52 (1H, d, J=12.5Hz, OCHH) 4.13 (1H, d, J=12.5 Hz, OCHH), 3.84 (1H, d, J=1.0 Hz, NCHPh), 3.68 (1H, d, J=1.5 Hz), 3.28 (1H, m, NCHCHO), 2.84 (1H, ddd, J=3.0, 12.5, 12.5 Hz, NCHH), 2.20 (1H, mc, NCH H), 1.8–1.98 (2H, m, CH$_2$), 1.64–1.78 (1H, m, CHH), 1.50–1.58 (1H, m, CHH); MS m/z 404 ((M+1)$^+$, 90%).

The oil was dissolved in ether to which was added excess ethereal hydrogen chloride. Upon standing a white solid crystallised. This was filtered and recrystallised from ethyl acetate-methanol to afford the title compound as white crystals: mp 200–203° C. $^1$H NMR (360 MHz, DMSO) δ7.95 (1H, s, ArH), 7.81 (2H, s, ArH), 7.37–7.47 (5H, m, ArH), 4.78 (1H, d, J=13.0 Hz, OCHH), 4.56 (1H, s, NC HPh), 4.32 (1H, d, J=13.0 Hz, OCHH), 3.96 (1H, s, NCHC HO), 3.10 (1H, t, J=13.0 Hz, NCHH), 2.23 (1H, d, J=13.0 Hz, NCHH), 1.64–2.00 (4H, m, CH$_2$×2); MS (CI$^+$) m/z 404 (M+1)$^+$, 90%); Found: C, 54.08; H, 4.47; N, 3.13. Calcd. for C$_{20}$H$_{20}$F$_6$NOCl.0.25H$_2$O: C, 54.06; H, 4.65; N, 3.15%.

DESCRIPTION 2

(2R*,3R*)-3- ((3,5-Bis(trifluoromethyl)phenyl) methyloxy)-1-(carbomethoxy)methyl-2-phenylypiperidine cis-3-((3,5-Bis(trifluoromethyl)phenyl)methyloxy)-2-phenyl pipeddine hydrochloride (Description 1, 1 g) was liberated from the hydrochloride salt by partitioning between ethyl acetate and 2M sodium hydroxide. The organic phase was washed successively with water, saturated brine, dried (MgSO$_4$) and evaporated in vacuo. To a solution of the residual off in tetrahydrofuran (20 ml) was added triethylamine (0.4 ml) and methyl bromoacetate (400 mg) and the solution was heated at reflux under an atmosphere of nitrogen for 16 h. To the cooled solution was added ethyl acetate and water and the organic phase washed further with water and dried (MgSO$_4$). After the solvent had been removed in vacuo the residue was chromatographed on silica gel eluting with ethyl acetate/petrolenm ether (3:10). The product was recrystallised from diethyl ether/petroleum ether to give the title compound, mp =81–83° C. Found: C, 57.35; H, 4.98; N, 2.84; C$_{23}$H$_{23}$F$_6$NO$_3$.0.1(H$_2$O) requires C, 57.71; H, 4.86; N, 2.93%. MS (CI$^+$) m/z=476 (M+H)$^+$.

DESCRIPTION 3

(+)-(2S,3S)-cis-3-((3,5-Bis(trifluoromethyl)phenvl) methyloxy)-2-phenylpiperidine hydrochloride salt a) The mixture of cis- and trans-isonaers of 3-hydroxy-2-phenylpiperidine (Description 1, (2b)) add 4-toluenesulfonic acid naonohydrate was crystallized from naethanol/ethyl acetate to give cis,3-hydroxy-2-phenylpiperidinium tosylate, mp 266°–267° C.

b) The tosylate salt (Description 3(a) above) was dissolved in a mixture of ethyl acetate and 10% aqueous Na$_2$CO$_3$ with warming. The organic phase was washed with saturated brine, dried (K$_2$CO$_3$) and evaporated to give crystalline cis-3-hydroxy-2-phenylpiperidine, mp 110°–110.5° C.

c) cis-3-Hydroxy-2-phenylpiperidine (Description 3b) and (−)dibenzoyltartrate were dissolved in methanol and crystallized by addition of ethyl acetate. The solid was recrystallised from hot methanol to give the hemi dibenzoyltartrate salt, mp 223°–224° C. This was liberated from the salt as described above to give the single enantiomer (+)-cis-3-hydroxy-2-phenylpiperidine, mp 93°–95° C. [α]$^{23}_D$=+98.5° (c=1, MeOH). The mother liquors were converted to the free base as described in Description 3b and crystallization using (+)dibenzoyltartrate in an analogous manner to that described above gave (−)-3-hydroxy-2-phenylpiperidine, mp 93°–95° C. [α]$^{23}_D$=−97.2° C. (c=1, MeOH).

d) (+)-cis-3-Hydroxy-2-phenylpiperidine was reacted according to the procedure detailed in Description 1c-e to give (+)-cis-3-((3,5-bis (trifluoromethyl)phenyl)methyloxy)-2-phenylpiperidine hydrochloride as a crystalline solid: mp 215°–216° C. [α]$_D$=+87.3° C. (c=1, MeOH). $^1$H NMR (360 MHz, DMSO-d$_6$) δ7.95 (1H, s, ArH), 7.81 (1H, s, ArH), 7.47 (2H, m, ArH), 7.37 (3H, m, ArH), 4.78 (1H, d, J=13.0 Hz, OCHH), 4.56 (1H, s, NCHPh), 4.32 (1H, d, J=13.0 Hz, OCHH), 3.96 (1H, s, NCHCHO), 3.10 (1H, t, J=13.0 Hz, NCHH), 2.23 (1H, d, J=13.0 Hz, NCHH), 2.00–1.64 (4H, m, CH$_2$×2); MS (CI$^+$) m/z 404 (M+1$^+$, 90%); Found: C, 54.52; H, 4.60; N, 3.11. Calcd. for C$_{20}$H$_{19}$F$_6$NO.HCl: C, 54.62; H, 4.58; N, 3.18%.

DESCRIPTION 4

(+)-(2S, 3S)-3-((3,5-Bis(trifluoromethyl)phenyl) methyloxy)-1-(carbomethoxy)methyl-2-phenylpiperidine The title cornhound was prepared from (+)-cis-3-((3,5-bis (trifluoromethyl)phenyl)methyloxy)-2-phenylpiperidine (Description 3) using the procedure detailed in Description 2: mp 60°–70° C. [α]$_D$=+132.3° (c=1, MeOH). $^1$H NMR (360 MHz, CDCl$_3$) δ1.57–1.63 (3H, m, CH$_2$+CHH), 2.04–2.17 (2H, m, CHH, CHHN), 3.07–3.10 (1H, m, NCHC HO), 3.20 (1H, d, J=17.0 Hz, NCHHCO$_2$CH$_3$), 3.31 (1H, d, J=17.0 Hz, NCHCH CO$_2$CH$_3$), 3.58 (3H, s, CH$_3$), 3.93 (1H, s, NCHPh), 4.07 (1H, d, J=12.0 Hz, OCHH), 4.49 (1H, d, J=12.0 Hz, OCHH), 7.28–7.34 (3H, m, ArH), 7.43–7.45 (2H, m, ArH), 7.54 (2H, s, ArH), 7.71 (1H, s, ArH). MS (CI$^+$) m/z 476 (M+1$^+$, 100%). Found: C, 58.31; H, 4.90; N, 2.94. Calcd. for C$_{23}$H$_{23}$F$_6$NO$_3$; 58.11; H, 4.88; N, 2.95%.

DESCRIPTION 5

(2R*,3R*)-3-((3,5-Bis(trifluoromethyl)phenyl) methyloxy)-1-(carboxymethyl)-2-phenylpiperidine.

The ester of Description 2 (4.98 g) was dissolved in anhydrous THF (80 ml) and an aqueous solution of potassinm hydroxide (1.76 g). The reaction was brought to reflux for 3 hrs and allowed to cool. The THF was removed in vacuo and the residue freeze dried, this afforded a yellow solid, which was dissolved in the minimum amount of water and the pH adjusted to 6.0 by careful addition of 1M HCl. A white precipitate was formed, this was filtered, re-dissolved in ethyl acetate and dried (MgSO$_4$). The solvent was removed in vacuo to afford a yellow solid (4.59 g). The product was recrystallised from ethyl acetate/petrol as the zwitterion: mp 172°–175° C. $^1$H NMR (360 MHz, DMSO) δ1.44–1.60 (2H, m, CH$_2$), 1.82–1.97 (1H, m, CHH), 2.12–2.24 (1H, m, CHH), 2.46–2.63(1H, m, CHH), 2.80 (1H, d, J=17.0 Hz, NCHH) 3.02–3.06 (1H, m, CHH) 3.12 (1H, d, J=17.0 Hz, NCHH), 3.57 (1H, s, CHO), 3.80 (1H, m, NCHPh), 4.09 (1H, d, J=13 Hz, OCHH), 4.63 (1H, d, J=13 Hz, OCHH), 7.22–7.40 (5H, m, Ar-H), 7.70 (2H, s, ArH), 7.93 (1H, s, ArH); MS(CI$^+$) m/z 462 (M$^+$+1, 30%); Found: C, 57.33; H, 4.59; N, 3.14. Calcd. for $C_{22}H_{21}F_6NO_3$: C, 57.26; H, 4.59; N, 3.04.

DESCRIPTION 6

(2S, 3S)-3-((3,5-Bis(trifluoromethyl)phenyl)methyloxy)-1-carboxymethyl)-2-phenyldiperidine The title compound was prepared from the compound of Description 4 using the procedure detailed in Description 5: MS(CI$^+$) m/z 462 (M$^+$+1).

EXAMPLE 1

(2R*,3R*)-3-((3,5-Bis(trifluoromethyl)phenyl)methyloxy)-2-phenyl-1-(N-(prop-2-ynyl)carboxamidomethyl)piperidine The product of Description 5 (1 g) was dissolved in anhydrous THF (40ml) under nitrogen. 1-Hydroxybenzotriazole hydrate (1.2 g), 1-(3-dimethylaminopropyl)-3-ethylcarbodiimide hydrochloride (1.66 g), triethylsmine (1.2 ml) and propargylomine (0.55 ml) were added and the reaction was allowed to stir overnight at room temperature. The solvent was removed in vacuo and the residual yellow oil dispersed between water and ethyl acetate. The organic layer was washed with 1M citric acid, water, sodium hydrogen carbonate, brine, dried (MgSO$_4$) and concentrated in vacuo to afford a yellow off. This was purified on silica using 50% ethyl acetate in petrol as eluant. The product was purified further by medium pressure chromatography eluting with 30% ethyl acetate in petrol to afford the title compound as a colourless off. $^1$H NMR (360 MHz, DMSO) δ1.54–1.68 (2H, m, CH$_2$), 2.00–2.34 (4H, m, NCHHCH$_2$+NHCH$_2$C≡CH), 2.55 (1H, d, J=16 Hz, NCHHCONH), 3.07 (1H, bd, NCHH), 3.20 (1H, d, J=16 Hz, NCHHCONH), 3.45 (1H, m, CHO), 3.59 (1H, m, CHPh), 4.00–4.18 (3H, m, OCHH+NHCH$_2$CCH), 4.48 (1H, d, J=12 Hz, OCHH), 7.13–7.40 (6H, m, ArH+NH), 7.55 (2H, s, ArH). 7.74 (H, s, ArH); MS (CI$^+$) 497 (M+1$^+$, 20%); Found: C, 59.81; H, 4.81; N, 5.54. Calcd. for $C_{25}H_{24}N_2O_2F_6$: C, 60.20; H, 4.85 ;N, 5.62%.

EXAMPLE 2

(2R*,3R*)-3-((3,5-Bis(trifluoromethyl)phenyl)methyloxy-1-(N-furfurylcarboxamidomethyl)-2-phenylpiperidine Following the method of Example 1, the product of Description 5 was reacted with furfurylamine to afford the title compound: mp 80°–83° C. Found: C, 59.83; H, 4.84; N, 5.32; Calcd. for $C_{27}H_{27}F_6N_3O_3$: C, 59.99; H, 4.85; N, 5.18%

EXAMPLE 3

(2R*,3R*)$_3$-((3,5-Bis(trifiuoromethyl)phenyl)methyloxy)-2-phenyl-1-(N-(3-pyridylmethyl)carboxamidomethyl)piperidine.

Following the method of Example 1, the product of Description 5 was reacted with 3-(aminomethyl) pyridine to give the title compound: mp 127°–130° C. Found: C, 60.75; H, 5.05; N, 7.34; Calcd. for $C_{28}H_{27}F_6N_3O_2$: C, 60.98; H, 4.93; N, 7.62%

EXAMPLE 4

(2R*,3R*)-3-((3,5-Bis(trifluoromethyl)phenyl)methyloxy)-1-(N-(2-methoxyethyl)carboxamidomethyl)-2-phenylpiperidinium hydrochloride Following the method of Example 1, the product of Description 5 was reacted with 2-methoxyethylamine to give the title compound after treatment with ethereal HCl: mp 146°–148° C. Found: C, 53.85; H, 5.37; N, 4.79; Calcd. for $C_{25}H_{28}F_6N_3O_3$ HCl: C, 54.11; H, 5.27; N, 5.05%.

EXAMPLE 5

(2R *,3R*)-3-((3,5-Bis(trifluoromethyl)phenyl)methyloxy)1-carboxyhydriazidomethyl)-2-phenylpiperidinium hydrochloride Hydrazine hydrate (3.0 ml) was added to a solution of the compound of Description 2 (2.95 g) in ethanol (80 ml). The solution was heated to reflux for 18 h after which the ethanol was removed in vacuo. The residue was extracted into ethyl acetate and the organic layer was washed with brine, dried (MgSO$_4$) and concentrated to give the title compound (2.79 g). This was dissolved in methanol (5 ml) and a methanolic solution of hydrogen chloride was added. Methanol was removed in vacuo and the salt was recrystallised from diethyl ether to give the hydrochloride salt. $^1$H NMR (360 MHz, DMSO) δ1.77–1.93 (2H, m, CH$_2$), 2.08–2.21 (1H, m, CH$_2$), 2.22–2.35 (1H, m, CH$_2$), 3,56 (1H, d, NCHHCH$_2$), 3.64 (1H, d, J=16.5 Hz, NCHHCO), 3.77 (1H, d, NCH HCH$_2$), 3.92 (1H, d, J=16.5 Hz, NCHHCO), 3.96 (1H, brs, CHO), 4.37 (1H, d, J=13.0 Hz, OCHH), 4.83 (1H, d, J=13.0 Hz, OCHH), 4.95 (1H, s, CHPh), 7.36–7.46 (3H, m, ArH), 7.53–7.62 (2H, brs, ArH), 7.95 (2H, s, ArH), 7.97 (1H, s, ArH); MS (CI)$^+$m/z 475.

EXAMPLE 6

(2S, 3S)-1-(N-Amidino(carboxamidomethyl))-3-((3,5-bis(trifiuoromethyl)phenyl)methyloxy-2-phenylniperidine Guanidine hydrochloride (600 mg) was added to a solution of sodium (150 mg) in methanol (30 ml) and the solution was heated at reflux for 30 min. To this solution was added the ester of Description 4 and the resulting solution was heated at reflux for 1 h. The solution was cooled, and concentrated in vacuo. The residue was dispersed between ethyl acetate and water. The organic phase was separated, dried (MgSO$_4$) and concentrated. The residue was purified by chromatography on alumina (grade III) using a gradient elution of 1–10% methanol in dichloromethane. This afforded the desired product which was recrystallised from ether/hexane: mp 159°–160° C. Found: C, 54.77; H, 4.99; N, 11.19: Calcd. for $C_{23}H_{24}F_6N_4O_2$: C, 54.98; H, 4.81; N, 11.15%.

EXAMPLE 7

(2S, 3S)-3-((3,5-Bis(trifiuoromethyl)phenyl)methyloxy)-2-phenyl-1-(N-methyl-N-(3-pyridylmethyl)carboxamidomethyl piperidinium hydrobromide (a) (N-(Chloroacetyl)-N-methylaminomethyl)pyridinium hydrochloride Chloroacetyl chloride (790 mg) was added dropwise to a chilled solution of 3-(N-methylaminomethyl)pyridine in dichloromethane (30 ml). The resulting solution was stirred at 5° C. for 2 h. Removal of solvent afforded the product as a white crystalline solid: mp 120°–121° C. $^1$H (360 MHz DMSO-$d_6$) 3.1 (3H, s, N$\underline{Me}$), 4.50 (2H, s, ClC$\underline{H_2}$CO), 4.75 (2H, s, N-C$\underline{H_2}$-pyridine), 8.01 (1H, dd, J=6.0, 5.5 Hz, ArH), 8.43 (1H, m, ArH), 8.89 (2H, m, ArH); MS m/z (CI$^+$) 199 (M$^+$+1).

(b) (2S, 3S)-3-((3,5-Bis(trifluoromethyl)phenyl)methyloxy)-2-phenyl-1-(N-methyl-N-(3-pyridylmethyl)carboxamidomethyl) piperidine dihydrobromide Diisopropylethylamine (4.3 ml) was added to a stirred suspension of 3-(N-(chloracetyl)-N-methylaminomethyl)pyridine hydrochloride (1.6 g) and the compound of Description 3 (3.6 g). The resulting solution was stirred at room temperature for 18 h. After this time the white precipitate was filtered off and the solvent removed under reduced pressure. The solid residue was taken up in water (50ml) and extracted into ethyl acetate (2×50ml). The organic extracts were combined, dried (MgSO$_4$), filtered and the solvent removed under reduced pressure. The product was isolated by flash chromatography on silica gel using 20% ethyl acetate in hexane as eluent. The isolated free base was treated with a solution of hydrogen bromide in ether, followed by recrystallisation from methyl-t-butyl ether to afford the product as an amorphous solid: mp 68°–70° C. $^1$H NMR (360 MHz, CDCl$_3$, free base), 1.6 (2H, m, C$\underline{H_2}$CH$_2$N), 2.1 (2H, m, C$\underline{H_2}$CH$_2$), 2.68 (3H, s, NC$\underline{H_3}$), 2.79 (2H, s, CH$_3$N—C$\underline{H_2}$), 3.15 (2H, m, C$\underline{H_2}$ NCH), 3,59 (1H, bs, NC$\underline{H}$-Ph), 4.08 (2H, m, C$\underline{H}$—O—CH$_2$Ar and C$\underline{HH}$—CO), 4.3 (1H, d, J=10.0 Hz, OC$\underline{HH}$—Ar), 4.60 (2H, m, CH$\underline{H}$CO and OCH$\underline{H}$—Ar), 7.1–7.25 (7H, m, Ar—H), 7.51 (2H, s, ArH), 7.63 (1H, s, ArH), 8.15–8.3 (2H, Ar—H): MS m/z (CI$^+$) 567 (M$^+$+1). Found: C, 46.63; H, 4.64; N, 5.46. Calcd. for C$_{29}$H$_{29}$F$_6$N$_3$O$_2$.2HBr.H$_2$O: C, 46.72; H, 4.46; N, 5.63%.

EXAMPLE 8

(2S, 3S)-3-((3,5-Bis(trifluoromethyl)phenyl)methyloxy)-1-(2-morpholino-2-oxo)ethyl-2-phenylpiperidinium hydrochloride The compound of Description 6 (2 g), triethylamine (2.42ml), morpholine (1.5 ml), hydroxybenzotriazole (2.35 g) and 1-(3-dimethylnminopropyl)-3-ethylcarbodimide hydrochloride (1.66 g) were suspended in dimethylformamide (25ml) and the reaction mixutre was allowed to stir under nitrogen for 12 h. The solvent was removed in vacuo and the residual yellow oil was dispersed between water and ethyl acetate. The organic layer was washed successively with 1M citric acid, water, sodium hydrogen carbonate solution, brine, then dried (MgSO$_4$) and concentrated in vacuo to afford a yellow oil. This was purified by chromatography on silica using 70% ethyl acetate in petrol as eluent. This afforded the title compound as a colourless oil. Treatment of this oil with ethereal hydrogen chloride afforded the hydrochloride salt which was recrystallised from ethyl acetate/petrol: mp 90°–91° C. $^1$H NMR (360 MHz, DMSO-$d_6$) δ1.49–1.52 (2H, m, CH$_2$), 1.89–1.90 (1H, m, C$_2$), 2.12–2.18 (1H, m, CH$_2$), 2.41–2.47 (1H, m, CH$\underline{H}$N), 2.76 (1H, d, J=15.0 Hz, NC$\underline{H}$HCO), 2.96–2.99 (1H, m, CH$\underline{H}$N), 3.16 (1H, d, J=15.0 Hz, NCH$\underline{H}$CO), 3.29–3.32 (2H, m, CH$_2$-morpholine), 3.43–3.48 (6H, m, CH$_2$-morpholine), 3,57 (1H, s, C$\underline{H}$O), 3.61 (1H, s, NC$\underline{H}$Ph), 4.15 (1H, d, J=13.0 Hz, OC$\underline{H}$H), 4.65 (1H, d, J=13.0 Hz, OCH$\underline{H}$), 7.24–7.28 (3H, m, ArH), 7.39–7.41 (2H, m, ArH), 7.76 (2H, s, ArH), 7.94 (1H, s, ArH); MS (CI$^+$) m/z 530 ((M+1)$^+$, 70%). Found: C, 53.82; H, 5.35; N, 4.90; Cl, 6.20; Calcd. for C$_{26}$H$_{28}$F$_6$N$_2$O$_3$.HCl.H$_2$O: C, 53.38; H, 5.34; N, 4.79; Cl, 6.06%.

EXAMPLE 9

(2S, 3S)-3-((3,5-Bis(trifluoromethyl)phenyl)methyloxy)-1-(2-oxo-2-piperidino)ethyl-2-phenylpiperidinium hydrochloride The title compound was prepared following the method described in Example 8, using piperidine as a starting material; this afforded a white crystalline material: mp 89°–91° C. $^1$H NMR (360 MHz, DMSO-$d_6$) δ0.85–0.92 (1H, m, C$\underline{H}$H), 1.08–1.14 (1H, m, CH$\underline{H}$), 1.25–1.34 (2H, m, CH$_2$), 1.38–1.46 (2H, m, CH$_2$), 1.76–1.88 (2H, m, CH$_2$), 2.20–2.32 (2H, m, CH$_2$), 2.49–2.51 (4H, m, 2×CH$_2$), 3.16–3.24 (1H, m, C$\underline{H}$HN), 3.40–3.48 (1H, m, CH$\underline{H}$N), 3.82 (1H, d, J=17.0 Hz, N—C$\underline{H}$HCO), 3.93 (1H, d, J=17.0 Hz, N—CH$\underline{H}$CO), 3.98 (1H, s, CHO), 4.43 (1H, d, J=13.0 Hz, OC$\underline{H}$H), 4.86 (1H, d, J=13.0 Hz, OCH$\underline{H}$), 5.07 (1H, s, NC $\underline{H}$Ph), 7.24–7.27 (3H, m, ArH), 7.41–7.44 (2H, m, ArH), 7.80 (2H, s, ArH), 7.95 (1H, s, ArH); MS (CI$^+$) m/z 529 ((M+1)$^+$, 100%).

EXAMPLE 10

(2S, 3S)-3-((3,5-Bis(trifluoromethyl)phenyl)methyloxy)-1-(2-oxo-2-(4-methylpiperazinyl))ethyl-2-phenylpiperidinium hydrochloride The title compound was prepared following the method described in Example 8 using N-methylpiperazine as a starting material; this afforded the product as a white powder. $^1$H NMR (360 MHz, DMSO-$d_6$) δ1.48–1.52 (2H, m, CH$_2$), 1.8–1.90 (1H, m, C$\underline{H}$H), 2.18–2.24 (1H, m, CH$_2$), 2.38–2.44 (1H, m, NC$\underline{H}$H), 2.50 (3H, s, CH$_3$), 2.71 (1H, d, J=14.0 Hz, C$\underline{H}$HCO), 2.94–2.97 (1H, m, NC$\underline{H}$H), 3.15 (1H, d, J=14.0 Hz, CH$\underline{H}$CO), 3.20–3.25 (2H, m, CHO), 3.25–3.31 (4H, m, NCH$_2$CH$_2$N), 3.42–3.57 (4H, m, NCH$_2$CH$_2$N), 4.15 (1H, d, J=13.0 Hz, OC$\underline{H}$H), 4.65 (1H, d, J=13.0 Hz, OCH$\underline{H}$), 7.24–7.26 (3H, m, ArH), 7.39–7.42 (2H, m, ArH), 7.76 (2H, s, ArH), 7.95 (1H, s, ArH); MS (CI$^+$) m/z 543 ((M+1)$^+$, 80%).

EXAMPLE 11

(2R*,3R*)-3-Benzyloxy-1-(2-morpholino-2-oxo)ethyl-2-phenylpiperidinium hydrochloride (a) Bromoacetylmorpholine Bromoacetylbromide (20.1 g) was added dropwise to a rapidly stirred solution of morpholine (17.4 g) in ether (200 ml). After stirring overnight, the mixture was washed with water (2×50 ml), dried (MgSO$_4$) and evaporated to afford a colourless oil. $^1$H NMR (360 MHz, CDCl$_3$) δ3.46 (2H, m, 2×C$\underline{H}$HN), 3.63 (2H, m, 2×CH$\underline{H}$N), 3.69 (4H, m, 2×CH$_2$O), 3.75 (2H, s, CH$_2$Br).

(b) (2R*, 3R*),3 Benzyloxy-1-(2-morpholino-2-oxo)ethyl-2-phenylpiperidiunium hydrochloride A mixture of the compound of Description 1 (139 mg), bromoacetylmorpholine (208 mg) and potassium carbonate (50 mg) in dimethylformamide (10ml) was heated to 100° C.

under N$_2$ for 5 h. The mixture was cooled, diluted with water (50 ml) and extracted with ethyl acetate (2×50 ml). The combined extracts were washed with brine (50 ml), dried (MgSO$_4$) and evaporated to afford a yellow oil. This was purified by column chromatography on silica eluting with ethyl acetate to afford a colourless oil. Fomation of the hydrochloride salt and recrystallisation from ethyl acetate/hexane afforded the title compound; mp 84°–85° C.

EXAMPLE 12

(2R*,3R*)-3-((3,5-Bis(trifluoromethyl)phenyl) methyloxy)-2-phenyl-1-(thiocarboxamidomethyl) piperidine (a) (2R*,3R*)-3-((3,5-Bis(trifiuoromethyl)phenyl)methyloxy)-1-(cyanomethyl)-2-phenylpiperidinium hydrochloride The compound of description 1 (5 g), potassium carbonate (1.7 g) and bromoacetonitrile (0.87ml) were suspended in dimethylformamide (15 ml) and the mixture was stirred under nitrogen at 60° C. for 3 h. The mixture was cooled, diluted with water (200 ml) and extracted with ethyl acetate (2×50 ml). The organic extracts were washed with brine, dried (MgSO$_4$) and evaporated, affording a brown oil. This was purified on silica using ethyl acetate in petrol (10%) as eluant. This afforded the product as a colourless oil. The hydrochloride salt was prepared by dissolution in ethereal hydrogen chloride and the salt was recrystallised from ether-hexane: mp 133°–134° C. $^1$H NMR (360 MHz, CDCl$_3$) δ1.75 (2H, mc, CHH), 1.90 (2H, mc, CHH), 2.31 (1H, mc, CHH), 2.71 (1H, mc, CHH), 3.19 (1H, mc, CH HN), 3.72 (1H, mc, CHHN), 3.81 (1H, d, J=17.5 Hz, NC HHCN), 3.86 (1H, s, CHO), 4.02 (1H, d, J=17.5 Hz, NCH HCN), 4.09 (1H, s, CHPh), 4.35 (1H, d, J=13.0 Hz, OC HH), 4.73 (1H, d, J=13.0 Hz, OCHH), 7.4 (3H, mc, ArH), 7.69–7.73 (5H, m, ArH); MS (CI$^+$) m/z 443 (M++1, 30%). Found: C, 54.87; H, 4.30; N, 5.66. Calcd. for C$_{22}$H$_{18}$F$_6$N$_2$O.HCl; C, 55.18; H, 4.42; N, 5.85%.

(b) (2R*,3R*)-3-((3,5-Bis(trifiuoromethyl)phenyl)methyloxy)-2-phenyl-1-(thiocarboxamidomethyl)piperidine The compound of (b) above (1 g) was dissolved in dimethylfomamide (anhydrous, 10 ml) and the solution was saturated with dry hydrogen chloride gas. The reaction was heated to 100° C. under nitrogen and thioacetamide (0.34 g) was added; this mixture was allowed to stir at 100° C. for 3 h. Dimethylformnmide was removed in vacuo. The residue was extracted with ethyl acetate and the organic layer was washed with aqueous sodium bicarbonate, brine, dried (MgSO$_4$) and concentrated in vacuo to afford a brown oil. This was purified on silica using a gradient elution of ethyl acetate in petrol (10–50%). The product was further purified by recrystallisation from ethyl acetate-petrol; mp 164°–166° C. $^1$H NMR (360 MHz, CDCl$_3$) δ1.56–1.70 (2H, m, CH$_2$), 1.96–2.10 (1H, m, CHH), 2.15–2.32 (2H, m, CHHN+CH H) 2.98–3.06 (1H, bd, NCHH), 3.09 (1H, d, J=18.0 Hz, C HHSNH$_2$), 3.50 (1H, d, J=18.0 Hz, NCHHCSNH$_2$), 3.50 (1H, s, CHO), 3.60 (1H, s, NCHPh), 4.04 (1H, d, J=12.0 Hz, OCHHAr), 4.47 (1H, d, J=12.0 Hz, OCHHAr), 7.26–7.36 (5H, m, CHPh), 7.53 (2H, s, Ar-H), 7.75 (H, s, Ar-H), 7.61 (1H, bs, NHH), 8.99 (1H, bs, NHH); MS (CI$^+$) m/z 477 (M$^+$+1, 15%); Found: C, 55.09; H, 4.58; N, 5.97. Calcd. for C$_{22}$H$_{22}$F$_6$N$_2$OS; C, 55.46; H, 4.65; N, 5.88.

EXAMPLE 13

(2S, 3S)-3-((3,5-Bis(trifluoromethyl)phenyl)methloxy)-2-phenyl-1-(N-(2-pyridylmethyl)carboxamidomethyl)piperidine The compound of Description 6 was reacted with 2-(aminomethyl)pyridine to afford the title compound: mp 112°–114° C. Found: C, 61.27; H, 5.12; N, 7.59. Calcd. for C$_{28}$H$_{27}$F$_6$N$_3$O$_2$. C, 60.98; H, 4.93; N, 7.62%. MS (CI$^+$) m/z 552 (M$^+$+1, 30%).

EXAMPLE 14

2-[(2S, 3S)-3-((3,5-Bis(trifluoromethyl)phenyl)methylory)-2-(diphenylmethylpyrrolidino]-N-(carbomethoxy) acetamidrazone (a) N-Carbomethoxy-2-chloroacetamidrazone Sodium methoxide (0.032 g) was added to a solution of chloroacetonitrile (1.26 ml) in anhydrous methanol (15 ml) at 0° C. The reaction mixture was stirred at room temperature for 0.5 h and then neutralised with acetic acid (0.034 ml). Methyl hydrazinocarboxylate (1.79 g) was added and the reaction mixture stirred at room temperature for 0.5 h. The solution was concentrated in vacuo to give the title compound as a white solid; mp 138°–140° C. MS (CI)$^+$m/z 166.

(b) (2S, 3S)-3-((3,5-Bis(trifluoromethyl)phenyl) methyloxy)-2-(diphenylmethyl)pyrrolidinium hydrochloride (i) N-t-Butyloxycarbonyl-(S)-diphenylalanal A solution of methyl sulfoxide (4.4ml) in dichloromethane (13 ml) was added dropwise to a cooled (−78° C.) solution of oxalyl chloride (4 ml) in dichloromethane (50 ml). After 15 min, a solution of N-t-butyloxycarbonyl-(S)-diphenylalanol (10 g) in dichloromethane (150 ml) was added dropwise at −30° C. The solution was allowed to stir for 30 min, triethylamine (17 ml) was added and the solution was allowed to warm to −10° C. Ice-water (200 ml) was added to the solution which was then poured onto hexane (600 ml). The organic phase was separated, washed successively with citric acid (200 ml), saturated aqueous sodium bicarbonate (2×150 ml), brine (1×150 ml) then dried (MgSO$_4$) and concentrated in vacuo to leave a white crystalline solid. $^1$H NMR (250 MHz, CDCl$_3$) δ1.42 (9H, s, C(CH$_3$)$_3$), 4.48 (1H, d), 4.86 (1H, d), 5.10 (1H, t), 7.26 (10H, m, ArH), 9.6 (1H, s, CHO).

(ii) N-t-Butyloxycarbonyl-1-(diphenylmethyl)-2-hydroxy-pent-4-enyl-1-amine

A solution of N-t-butyloxycarbonyl-(S)-diphenylalanal (10.9 g) in tetrahydrofuran (60ml) was added dropwise to a solution of allyl magnesium chloride (2M in tetrahydrofuran, 36 ml) at −10° C. After 30 min. the mixture was poured onto ice-cold saturated aqueous ammonium chloride and the resulting mixture was extracted with ethyl acetate (3×150 ml). The combined organic extracts were washed with brine (1×100 ml), then dried (MgSO$_4$) and concentrated in vacuo. The residue was purified by chromatography on silica gel using hexane in ethyl acetate (gradient elution of 9:1 to 4:1) as eluant to afford the compound as a white solid. $^1$H NMR (360 MHz, CDCl$_3$) δ1.42 (9H, s, (CH$_3$)$_3$), 2.22 (2H, m), 2.68 (3H, brs), 3.48 (t), 3,57 (1H, m), 3.86 (1H, s), 4.07 (d, J=11 Hz), 5.04 (1H, m), 5.71 (1H, m), 6.97–7.36 (10H, m, ArH).

(iii) 2-((3,5-Bis(trifluoromethyl)phenyl)methyloxy)-N-t-butyloxycarbonyl-1-(diphenylmethyl)-pent-4-enyl-1- amine Sodium hydride (80% in oil, 0.53 g) was added to a solution of 3,5-bis(trifiuoromethyl)benzyl bromide (5 ml) and the compound of (13b) above (5 g) in dimethylformamide (8 ml). After stirring for 1 h water (80 ml) was added and the mixture was extracted with ethyl acetate (3×100 ml). The combined organic extracts were washed with brine (1×100 ml) then dried (MgSO$_4$) and concentrated to leave an oil which was purified on silica using hexane in ethyl acetate as eluant (gradient elution of 97:3 to 4:1). This afforded the title compound as a colourless oil. $^1$H NMR (360 MHz, CDCl$_3$) δ1.25 (s), 1.30 (s), 2.35 (m), 3.31 (m), 3.40 (dd, J=5.2, 8.3 Hz), 3.97 (d), 4.27 (d), 4.38 (m), 4.65 (m), 4.85 (d), 5.16–5.02 (m), 5.77 (m), 7.35–7.13 (m), 7.76 (s), 7.85 (s).

(iv) (2S, 3S)-3-((3,5-Bis(trifluoromethyl)phenyl) methyloxy-2-(diphenylmethyl)pyrrolidinium hydrochloride A solution of the compound of (c) above (5.2 g) in dichloromethane (40 ml) and methanol (40 ml) was treated with a stream of ozone in oxygen at −78° C. for 1 h. Methyl sulfide (3 ml) was added and the mixture was warmed to 23° C. and concentrated in vacuo. The residue was dissolved in chloroform (50 ml), triethylsilane (5.6 ml) was added followed by dropwise addition of a solution of trifluoroacetic acid (6.9 ml) in chloroform (5 ml). After 1 h the solvent was evaporated in vacuo and trifluoroacetic acid (10 ml) was added to the residue. After stirring for 30 min the mixture was concentrated in vacuo and the residue was partitioned between dichloromethane and saturated aqueous sodium bicarbonate. The organic layer was dried (K$_2$CO$_3$) and concentrated to leave a broom oil. This was purified on silica gel eluting with dichloromethane/methanol (99:1) to provide the title compound as the free base. This was converted to the salt by treatment with methanolic hydrogen chloride: mp >230° C. [a]$^{23}$$_D$=+46.6° C. (c=1, CH$_3$OH). Found: C, 59.95; H, 4.74; N, 2.63%. Calcd. for C$_{26}$H$_{23}$F$_6$NO.HCl.0.2H$_2$O: C, 60.11; H, 4.73; N, 2.70%.

(c) The compound of (b) above (155 mg) was stirred with N-carbomethoxy-2-chloroacetamidrazone (a) (0.3 g) in dimethylformamide (5 ml) in the presence of potassium carbonate (260 mg) at 70° C. for 14 h. After cooling, the material was partitioned between ethyl acetate and water. The organic layer was washed with brine, dried (MgSO$_4$) and filtered. The solvent was evaporated and the residue was purified by chromatography on silica using 5% methanol in ethyl acetate as eluant. $^1$H NMR (360 MHz, CDCl$_3$) δ1.93 (2H, m), 2.60 (1H, m), 2.68 (1H, d, J=14 Hz), 2.96 (1H, d, J=14 Hz), 3.16 (1H, m), 3.70 (1H, m), 3.74 (3H, s), 4.09 (1H, m), 4.28 (2H, m), 4.66 (1H, brs), 7.35–7.11 (10H, m), 7.52 (2H, s), 7.77 (1H, s).

EXAMPLE 15

(2S, 3S)-3-(3,5-Bis(trifluoromethyl)phenyl)methyloxy-1-bis(carbonmethoxy)methyl-2-phenylpineridine The compound of Description 3 (0.439 g) was dissolved in dimethylformamide (3 ml) and dimethyl bromomalonate (0.274 g) and potassium carbonate were added. The mixture was heated at 60° C. overnight. The mixture was diluted with water and extracted into ethyl acetate. The organic phase was washed with water, dried (MgSO$_4$) and evaporated. The residue was purified by chromatography on silica using gradient elution of 5–20% ethyl acetate in hexane. This afforded the product as a clear oil. $^1$H NMR (360 MHz, CDCl$_3$) δ1.55–161 (2H, m), 2.04–2.17 (2H, m), 2.68–2.74 (1H, m), 3.37–3.41 (1H, m), 3,53 (1H, brs), 3.67 (3H, s, CH$_3$), 3.71 (3H, s, CH$_3$), 3.97 (1H, d, J=2 Hz), 4.02 (1H, d, J=12.5 Hz, OCHH), 4.26 (1H, s), 4.44 (1H, d, J=12.5 Hz, OCHH), 7.25–7.34 (3H, m, ArH), 7.40–7.42 (2H, m, ArH), 7.51 (2H, s, ArH), 7.71 (1H, s, ArH).

EXAMPLE 16

(2S, 3S)-3-(3,5-Bis(trifluoromethyl)phenyl)methyloxy)-1-bis(carboxamido)methyl-2-phenylpiperidinium hydrochloride (a) 2-Bromomalonamide 2-Cyanoacetamide (5 g) was dissolved in glacial acetic add (50 ml) and stirred under nitrogen. Bromine (9.5 g) was dissolved in acetic acid and added dropwise to the solution; after 2 h the mixture was evaporated to afford a white slurry. The title compound was recrystallised from ethanol. MS (CI$^+$) m/z 181 (M+1$^+$, 20%).

(b) (2S, 3S)-3-(3,5-Bis(trifluoromethyl)phenyl)methyloxy)-1-bis(carboxamido)methyl-2-phenylpiperidinium hydrochloride The compound of Description 3 (0.65 g) was dissolved in dimethylformamide (5 ml) under nitrogen and potassium carbonate (0.199 g) and 2-bromomalonamide (0.35 g) were added. The reaction mixture was stirred at 60° C. for 3 h. The compound was isolated following the procedure described in Example 15 and was purified by chromatography on silica using 4% methanol in dichloromethane as eluant to afford a white solid.

Treatment with ethereal hydrogen chloride afforded the title compound: mp 189°–194° C. $^1$H NMR (360 MHz, CDCl$_3$) δ1.56–1.74 (2H, m, NCH$_2$CH$_2$CH$_2$), 1.94–2.10 (1H, m, NCH$_2$CHH), 2.15–2.24 (1H, m, NCH$_2$CHH), 2.75–2.86 (1H, m, NCHH), 2.97–3.07 (1H, m, NCHH), 3.60 (H, bs, CHO, 3.85 (1H, bs, NCHPh), 4.13 (1H, d, J=12 Hz, OCHHAr), 4.50–4.60 (2H, m, NCH(CONH$_2$)$_2$ +OCHHAr), 5.44 (1H, bs, NH), 5.71 (1H, bs, NH), 7.27–7.37 (3H, m, ArH), 4.43–7.50 (2H, m, ArH), 7.62 (2H, s, ortho H's), 7.76 (1H, s, para H's), 8.01–8.25 (2H, m, NH+NH). MS (CI$^+$) m/z 504 (M+1$^+$, 30%). C$_{23}$H$_{23}$N$_3$O$_3$F$_6$ HCl, requires C, 51.17; H, 4.48; N, 7.78. Found: C, 51.00; H, 4.27; N, 7.67.

EXAMPLE 17

(2S, 3S)-3-(3,5,Bis(trifluoromeyl)phenyl)methyloxy)-1-(N-methanesulfonyl)carboxamidomethyl)-2-phenylpiperidine (a) N-Bromoacetylmethanesulfonamide Sodium hydride (1.68 g×60%) was added to a stirred solution of methanesulfonamide (2.0 g) in dry tetrahydrofuran (20 ml) at room temperature. The resulting solution was stirred at room temperature for 1 h, at which time it was treated with a solution of bromoacetyl bromide (4.2 g) in dry tetrahydrofuran (10 ml). After 1 h the solvent was removed under reduced pressure and the residue taken up in water and acidified to pH3. The acidic solution was extracted into ethyl acetate, dried (MgSO$_4$), filtered and the solvent removed under reduced pressure. Recrystallisation from isopropanol afforded the product as white needles: mp 112°–114° C.

(b) (2S, 3S)-3-(3,5-Bis(trifluoromethyl)phenyl)methyloxy)-1-(N-methanesulfonyl)carboxamidomethyl)-2-phenylpiperidine Diisopropylethylamine (187 mg) was added to a stirred solution of N-bromoacetylmethanesulfonamide (42 mg) and the compound of Description 3 (300 mg) in dry acetonitrile (10ml). The resulting solution was stirred for 18 h at room temperature. Solvent was removed under reduced pressure and the residue partitioned between ethyl acetate and water. The organic layers were separated, dried (MgSO$_4$), filtered and the solvent removed under reduced pressure. Recrystallisation from ether/hexane afforded the product as a white powder: mp 127°–130° C. C$_{23}$H$_{24}$N$_2$O$_4$F$_6$ 0.25H$_2$O requires C, 50.87; H, 4.55; N, 5.16. Found: C, 50.73; H, 4.38; N, 5.07%. The following examples illustrate pharmaceutical compositions according to the invention.

EXAMPLE 18A

A Tablets containing 1–25 mg of compound

|  | Amount mg | | |
|---|---|---|---|
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 18B

B Tablets containing 26–100 mg of compound

|  | Amount mg | | |
|---|---|---|---|
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 19

Parenteral injection

|  | Amount mg |
|---|---|
| Compound of formula (I) | 1 to 100 mg |
| Citric Acid Monohydrate | 0.75 mg |
| Sodium Phosphate | 4.5 mg |
| Sodium Chloride | 9 mg |
| Water for Injections | to 1 ml |

The sodium phosphate, citric acid monohydrate and sodium chloride are dissolved in a portion of the water. The compound of formula (I) is dissolved or suspended in the solution and made up to volume.

EXAMPLE 20

Topical formulation

|  | Amount mg |
|---|---|
| Compound of formula (I) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

We claim:

1. A compound of formula (I), or a salt of prodrug thereof:

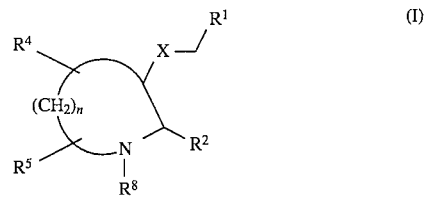

wherein n is 1, 2 or 3;

X represents O or S;

$R^1$ represents phenyl optionally substituted by 1, 2 or 3 groups selected from $C_{1-6}$alkyl, $C_{2-6}$ alkenyl, $C_{2-6}$alkynyl, halo, cyano, nitro, trifluoromethyl, trimethylsilyl, —$OR^a$, $SR^a$, $SOR^a$, $SO_2R^a$, —$NR^aR^b$, —$NR^aCOR^b$, —$NR^aCO_2R^b$, —$CO_2R^a$ and —$CONR^aR^b$;

$R^2$ represents aryl selected from phenyl and naphthyl; heteroaryl selected from indazolyl, thienyl, furyl, pyridyl, thiazolyl, tetrazolyl and quinolyl; benzhydryl; or benzyl; wherein each aryl or heteroaryl moiety may be substituted by $C_{1-6}$alkyl, $C_{1-6}$alkoxy, halo or trifluoromethyl;

$R^4$ and $R^5$ may be present on any available carbon atom of the azacyclic ring and each independently represent H, halo, $C_{1-6}$alkyl, oxo, $CH_2OR^a$, $CO_2R^a$ or $CONR^aR^b$;

$R^8$ represents $C(COOR^a)_2$, $C(CONR^aR^b)_2$ or $C_{1-6}$alkyl substituted by $C(=NR^a)NR^bNR^cCO_2R^d$, $CONHNR^aR^b$, $C(S)NR^aR^b$, $CONR^aC_{1-6}$alkyl$R^{12}$, $CONR^{13}C_{2-6}$alkynyl, $CONR^{13}C_{2-6}$alkenyl, $COCONR^aR^b$, $CONR^aC(NR^b)NR^cR^d$, $CONR^{13}SO_2R^a$, $SO_2NR^{13}COR^a$, $CONR^a$heteroaryl or $COR^q$;

$R^a$, $R^b$, $R^c$ and $R^d$ each independently represent H, $C_{1-6}$alkyl, phenyl or trifluoromethyl, $R^{12}$ represents $OR^a$, $CONR^aR^b$ or heteroaryl;

$R^{13}$ represents H or $C_{1-6}$alkyl; and $R^q$ represents a group

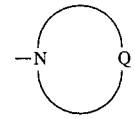

where Q represents the residue of a non-aromatic azacyclic or azabicyclic ring system, which residue may contain, in addition to the nitrogen atom through which the ring is linked to the carbonyl moiety of the group $COR^q$, a further heteroatom selected from O and S, or a group $NR^{18}$, where $R^{18}$ is H or $C_{1-6}$alkyl.

2. A compound as claimed in claim 1 wherein $R^4$ and $R^5$ each independently represent H, halo, $C_{1-6}$alkyl, oxo, $CO_2R^{10}$ or $CONR^{10}R^{11}$; $R^8$ represents $C_{1-6}$alkyl substituted by a group selected from $CONHNR^aR^b$, $C(S)NR^aR^b$, $CONR^aC_{1-6}$alkyl$R^{12}$, $CONR^{13}C_{2-6}$alkynyl, $CONR^{13}C_{2-6}$alkenyl, $COCONR^aR^b$, $CONR^aC(NR^b)NR^aR^b$, and $CONR^a$heteroaryl; or a salt or prodrug thereof.

3. A compound as claimed in claim 1 of formula (Ia):

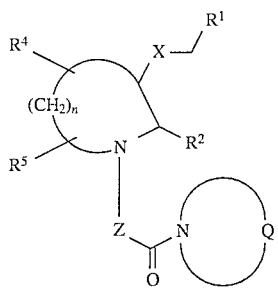

wherein n, X, R$^1$ and R$^2$ are as defined for formula (I); Q is the residue of an azacyclic or a bridged azabicyclic ring system;

Z represents an alkyl chain of 1, 2, 3, 4, 5 or 6 carbon atoms; and

R$^4$ and R$^5$ each independently represent H, halo, C$_{1-6}$alkyl, oxo, CO$_2$R$^a$ or CONR$^a$R$^b$; or a salt or prodrug thereof.

4. A compound as claimed in claim 1 wherein R$^8$ represents C(COO(C$_{1-6}$alkyl))$_2$, C(CONH$_2$)$_2$ or C$_{1-6}$alkyl substituted by C(=NH)NHNHCO$_2$C$_{1-6}$alkyl, CONHNH$_2$, COCONH$_2$, CONHC(NH)NH$_2$, CSNH$_2$, CONR$^{13}$C$_{2-6}$alkynyl, COR$^9$C$_{1-6}$alkylC$_{1-6}$alkoxy, CONHSO$_2$C$_{1-6}$alkyl, CONR$^a$C$_{1-6}$alkylheteroaryl, CONR$^a$-heteroaryl or COR$^q$.

5. A compound as claimed in claim 1 wherein n is 3.

6. A compound as claimed in claim 1 wherein X is O.

7. A compound as claimed in claim 1 wherein R$^1$ represents phenyl substituted by 1, 2 or 3 groups selected from C$_{1-4}$alkyl, trifluoromethyl and halo.

8. A compound as claimed in claim 1 wherein R$^2$ represents benzhydryl or phenyl optionally substituted by halo.

9. A compound selected from
(2R*, 3R*)-3-((3,5-bis(trifluoromethyl)phenyl)methyloxy)-2-phenyl-1-(N-(prop-2-ynyl)carboxamidomethyl)piperidine;
(2R*, 3R*)-3-((3,5-bis(trifluoromethyl)phenyl)methyloxy)-1-(N-furfuryl)carboxamidomethyl)-2-phenylpiperidine;
(2R*, 3R*)-3-((3,5-bis(trifluoromethyl)phenyl)methyloxy)-2-phenyl-1-(N-(3-pyridylmethyl)carboxamidomethyl) piperidine;
(2R*, 3R*)-3-((3,5-bis(trifluoromethyl)phenyl)methyloxy)-1-(N-(2-methoxyethyl)carboxamidomethyl)-2-phenyl piperidine;
(2R*, 3R*)-3-((3,5-bis(trifluoromethyl)phenyl)methyloxy)-1-(carboxyhydrazidomethyl)-2-phenylpiperidine;
(2S, 3S)-1-(N-amidino(carboxamidomethyl))-3-((3,5-bis-(trifluoromethyl)phenyl)methloxy)-2-phenylpiperidine;
(2S, 3S)-3-((3,5-bis(trifluoromethyl)phenyl)methyloxy)-2-phenyl-1-[N-methyl-N-((3-pyridylmethyl) carboxamidomethyl)]piperidine;
(2S, 3S)-3-((3,5-bis(trifluoromethyl)phenyl)methyloxy)-1-(2-morpholino-2-oxo)ethyl-2-phenylpiperidine;
(2S, 3S)-3-((3,5-bis(trifluoromethyl)phenyl)methyloxy)-1-(2-oxo-2-piperidino)ethyl-2-phenylpiperidine;
(2S, 3S)-3-((3,5-bis (trifluoromethyl)phenyl)methyloxy)-1-(2-oxo-2-(4-methylpiperazinyl))ethyl-2-phenylpiperidine;
(2R*, 3R*)-3-benzyloxy-1-(2-morpholino-2-oxo)ethyl-2-phenylpiperidine;
(2R*, 3R*)-3-((3,5-bis(trifluoromethyl)phenyl)methyloxy)-2-phenyl-1-(thiocarboxamidomethyl)piperidine;
(2S, 3S)-3-((3,5-bis(trifluoromethyl)phenyl)methyloxy)-2-phenyl-1-(N-(2-pyridylmethyl)carboxamidomethyl) piperidine;
2-[(2S, 3S)-3-((3,5-bis(trifluoromethyl)phenyl)methyloxy)-2-(diphenylmethyl)pyrrolidino]-N-(carbomethoxy)acetamidrazone;
(2S, 3S)-3-((3,5-bis(trifluoromethyl)phenyl)methyloxy)-1-bis(carbomethoxy)methyl-2-phenylpiperidine;
(2S, 3S)-3-((3,5-bis(trifluoromethyl)phenyl)methyloxy)-1-bis(carboxamido)methyl-2-phenylpiperidine;
(2S, 3S)-3-((3,5-bis(trifluoromethyl)phenyl)methyloxy)-1-(N-methanesulfonyl)carboxamidomethyl)-2-phenylpiperidine; and salts and prodrugs thereof.

10. A pharmaceutical composition comprising a compound as claimed in claim 1 in association with a pharmaceutically acceptable carrier.

11. A method for the treatment or prevention of a physiological disorder associated with an excess of tachykinins, which method comprises administration to a patient in need thereof of a tachykinin-reducing amount of a compound according to claim 1.

12. A method according to claim 11 for the treatment or prevention of pain or inflammation.

13. A method according to claim 11 for the treatment or prevention of migraine.

14. A method according to claim 11 for the treatment or prevention of arthritis.

\* \* \* \* \*